Nov. 10, 1964 C. G. KLEHM Plant Pat. 2,451
PEONY PLANT
Filed July 1, 1963
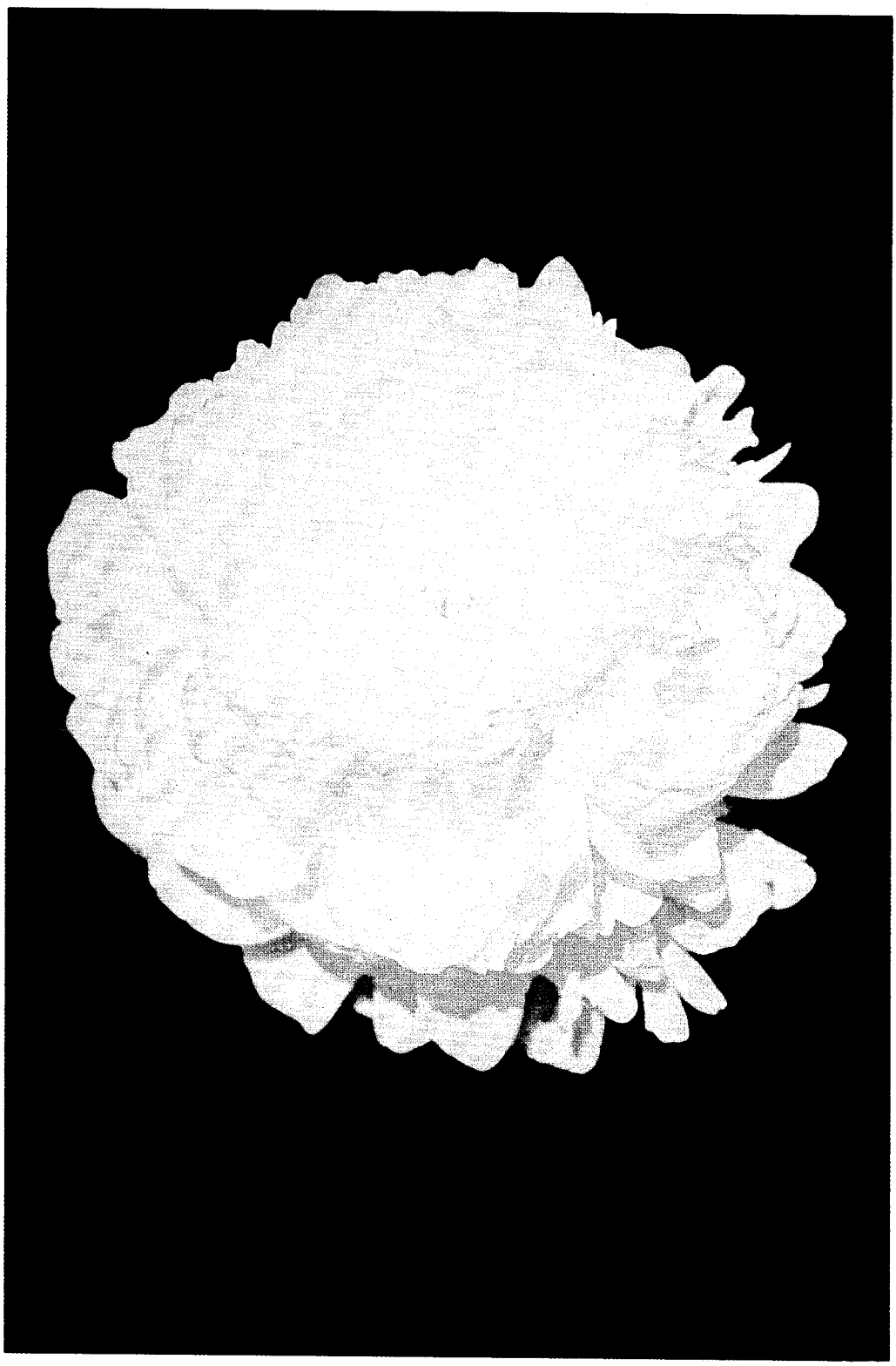

United States Patent Office

Plant Pat. 2,451
Patented Nov. 10, 1964

2,451
PEONY PLANT
Carl G. Klehm, 6 E. Algonquin Road,
Arlington Heights, Ill.
Filed July 1, 1963, Ser. No. 292,171
1 Claim. (Cl. Pit.—68)

The present invention relates to a new variety and strain of peony plant, especially characterized by the extremely large size of the bloom; the unusually clean, glistening, Cream White color of the strain which is enhanced by the reflection of light from concealed golden stamens located in the center of the bloom; the robustness of the plant; and its outstanding bright green foliage that makes it particularly adaptable for landscape planting.

This peony plant was originated by me at my nursery in Arlington Heights, Illinois, from a cross between Alice Harding, the pollen parent (not patented); and Mons. Jules Elie, the seed parent (not patented); by the processes of hand pollination. This peony plant was asexually reproduced by me in Arlington Heights, Illinois, by root division. Thousands of seedlings were developed as a result of this cross and, from these thousands, this particular peony plant was selected. It took seven years for the plant to produce its first bloom. The bloom of the plant has been under constant observation for seventeen years.

The peony plant derives its outstanding dark green foliage, exceptional resistance to bacterial diseases, strength of stem and vigorous growth properties from its seed parent, Mons. Jules Elie. It derives its outstanding color characteristics and form of flower from its pollen parent, Alice Harding.

The peony plant forming the subject matter of this application is considered novel with respect to heartiness, size, health, rich dark green color of foliage, color of flower, non-lanceolated guard petals, and resistance to disease.

It is a marked characteristic of this peony plant that the fully open bloom is extremely large, being 9½" in diameter, under normal growth conditions. The bloom is a full, double rose-type, with hidden golden stamens that light up the center, but has no carpels. It is a clean, glistening Cream White, with the center of the bloom having a distinctive brightness due to the reflection of light from the hidden golden stamens.

This peony plant is especially suitable for garden growing and landscape planting due, particularly, to the exceptional color and size of the bloom and its outstanding bright green foliage.

The accompanying drawing shows a view of an individual flower, in color as nearly true as reasonably possible in a color illustration of this character.

As a convenient summary, the following detailed description of this new peony plant is given with color terminology generally in accordance with Maerz and Paul's "Dictionary of Color" 1950 Edition, except where general color terms are used:

Parentage:

*Seed parent.*—Mons. Jules Elie, from which this new variety obtains its outstanding dark green foliage that is extremely resistant to bacterial diseases; the exceptional supporting strength of the stem, and the vigorous growth-qualities of the plant.

*Pollen parent.*—Alice Harding, from which this variety obtains its outstanding characteristics of color and form of flower.

*Flower*

Blooming habit: Annually.

Bud:

*Size.*—Very large.
*Form.*—Smooth, even and round.
*Color.*—Cream White with hidden golden stamens.
*Sepals.*—Smooth green, wrapped tightly around bud.
*Calyx.*—Polysepalous.
*Peduncle.*—None.
*Opening.*—Unfailing opening qualities—a very dependable performer.

Bloom:

*Size.*—Very large, average size when fully expanded, 9½" under normal growth conditions.
*Borne.*—Singly, one main flower bud per stem with 3 to 4 axillary buds.
*Stems.*—Long, strong, approximately 31" in height.
*Form.*—Rose type with 3 to 4 rows of guard petals.
*Petalage.*—Very double.
*Color.*—Cream White with hidden golden stamens generally within the range shown in Plate 10, rows 9 and 10 and items F through L.
*Variegations.*—None.
*Discoloration.*—None.

Petals:

*Texture.*—Thick, not affected by wet or hot weather.
*Appearance.*—Inside and outside, satiny.
*Form.*—Smooth—not lanceolated.
*Arrangement.*—Imbricated (double), many petaloids in center.
*Persistence.*—Drop off cleanly.
*Fragrance.*—Mildly scented.
*Lastingness.*—On the plant, very long.

Genital organs:

*Stamens, anthers.*—Golden yellow.
*Stamens, filaments.*—⅝" long.
*Pollen.*—Yes.
*Styles.*—None, complete petalody.
*Stigmas.*—None, complete petalody.
*Ovaries.*—None, complete petalody.

Fruit: None.

*Plant*

Form: Bush.

Growth: Vigorous, strong.

Foliage:

*Leaflets.*—Five.
*Size.*—Medium.
*Quantity.*—Above normal.
*Color.*—Normal rich dark green, of lactiflord type, beginning approximately 5" from ground and extending to bloom.
*Shape.*—Elliptically acute.
*Texture.*—Upper side, glossy with pronounced veins, underside, smooth with pronounced veins.
*Edge.*—Smooth.
*Serration.*—None.
*Leaf stem.*—Color—normal medium green.
*Stipules.*—None.
*Disease resistance.*—Exceptionally resistant to leaf blotch as observed for many years at Arlington Heights, Illinois. This was observed during the blooming season and in the fall of the year with notations of these observations being kept in a book used for this purpose.

I claim:

A new and distinct variety of peony plant characterized by its extremely large size of bloom, its distinct color, and the robust heartiness of the plant as shown and described herein.

No references cited.